US009216239B2

(12) United States Patent
Rubin

(10) Patent No.: US 9,216,239 B2
(45) Date of Patent: Dec. 22, 2015

(54) MEDICAL DEVICE FOR INTRA-LUMENAL DELIVERY OF PHARMACEUTICAL AGENTS

(76) Inventor: Leo Rubin, Suffern, NY (US)

( * ) Notice: Subject to any disclaimer, the term of this patent is extended or adjusted under 35 U.S.C. 154(b) by 1855 days.

(21) Appl. No.: 11/055,465

(22) Filed: Feb. 10, 2005

(65) Prior Publication Data

US 2010/0161038 A9    Jun. 24, 2010

Related U.S. Application Data

(63) Continuation-in-part of application No. 10/518,109, filed as application No. PCT/US03/18059 on Jun. 10, 2003, now abandoned, and a continuation of application No. 10/166,059, filed on Jun. 10, 2002, now abandoned.

(60) Provisional application No. 60/296,896, filed on Jun. 8, 2001, provisional application No. 60/299,867, filed on Jun. 21, 2001.

(51) Int. Cl.
  *A61L 31/16*  (2006.01)
  *A61L 29/14*  (2006.01)
  *A61L 29/16*  (2006.01)
  *A61L 31/14*  (2006.01)
  *A61M 25/00*  (2006.01)

(52) U.S. Cl.
  CPC .............. *A61L 31/16* (2013.01); *A61L 29/148* (2013.01); *A61L 29/16* (2013.01); *A61L 31/148* (2013.01); *A61L 2300/252* (2013.01); *A61L 2300/416* (2013.01); *A61M 2025/0057* (2013.01)

(58) Field of Classification Search
  CPC ................... A61L 2300/416; A61L 2300/252
  See application file for complete search history.

(56) References Cited

FOREIGN PATENT DOCUMENTS

WO     WO 91/17789     11/1991
WO     WO 99/30684     *  6/1999

OTHER PUBLICATIONS

Heldman et al. "Paclitexal Stent Coating Inhibits Neotimal Hyperplasia at 4 Weeks in a Porcine Model of Coronary Restenosis," Circulation, 2001, 103, 2289-95.*
Rowinsky & Donehower "Paclitaxel (Taxol)," New England J. Med., 1995, 332, 1004-14.*
Abou-Chebel et al. "Drug-Eluting Stents for the Treatment of Intracranial Atherosclerosis, Initial Experience and Midterm Angiographic Follow-up," Stroke, 2005, 36, e165-e168.*
Chamberlain & Kormanik "Salvage chemotherapy with paclitaxel for recurrent oligodendrogliomas," J. Clin. Oncol., 1997, 15, 3427-32, abstract only.*
Gelber et al. "A Lipophilic Vasoactive Intestinal Peptide Analog Enhances the Antiproliferative Effect of Chemotherapeutic Agents on Cancer Cell Lines," Cancer, 2001, 92, 2172-2180.*

* cited by examiner

*Primary Examiner* — Christina Bradley
(74) *Attorney, Agent, or Firm* — Hoxie & Associates, LLC

(57) ABSTRACT

The present invention relates to intra-lumenal drug delivery devices. The device, such as a stent, is coated or impregnated with a pharmaceutical agent suitable for use in treatment of restenosis, pulmonary hypertension, and cancer. Suitable pharmaceutical agents include vasodilators and chemotherapeutics.

12 Claims, No Drawings

MEDICAL DEVICE FOR INTRA-LUMENAL DELIVERY OF PHARMACEUTICAL AGENTS

CROSS-REFERENCE TO RELATED APPLICATIONS

This application is a continuation-in-part of U.S. application Ser. No. 10/518,109, filed Dec. 10, 2004, which is the National Phase of PCT/US03/18059, filed Jun. 10, 2003, which is a continuation of U.S. application Ser. No. 10/166,059, filed Jun. 10, 2002, which claims the benefit of U.S. Provisional Application No. 60/296,896 filed Jun. 8, 2001 and U.S. Provisional Application No. 60/299,867, filed Jun. 21, 2001.

FIELD OF THE INVENTION

The present invention relates to devices for intra-lumenal drug delivery. The devices are particularly useful for local delivery of therapeutic substances such as chemotherapeutics, platelet inhibitors, smooth muscle inhibitors and vasodilators. Such therapeutic substances can be used in treating restenosis, pulmonary hypertension and other circulatory disorders. The device is coated or impregnated with the pharmaceutical substance and can be permanent or biodegradable.

BACKGROUND OF THE INVENTION

Restenosis

Stenosis is the narrowing of the blood vessel lumen. In the case of the heart, stenosis of cardiac circulation can lead to acute infarction with subsequent ischemia. Stenosis is frequently treated with angioplasty. Neointimal formation after stent implantation can cause luminal narrowing called restenosis. Restenosis is induced by initial platelet adhesion and thrombus formation followed by immunocytic adhesion on the stent surface and injured vessel wall. The thrombus then releases factors that activate the proliferation of smooth muscle cells.

While percutaneous transluminal angioplasty (PTA), a method of expanding a blood vessel blocked by plaque, presently enjoys wide use, it suffers from two major problems. First, the blood vessel may suffer acute occlusion immediately after or within the initial hours after the dilation procedure. The second major problem encountered in PTA is the re-narrowing of an artery after an initially successful angioplasty. This re-narrowing is referred to as "restenosis" and typically occurs within the first six months after angioplasty. Restenosis is believed to arise through the proliferation and migration of smooth muscle cells arterial wall, as well as through geometric changes in the arterial wall referred to as "remodeling." It has similarly been postulated that the delivery of appropriate agents directly into the arterial wall could interrupt the cellular and/or remodeling events leading to restenosis. However, the results of attempts to prevent restenosis in this manner have been mixed.

A device such as an intravascular stent can be a useful adjunct to PTA, particularly in the case of either acute or threatened closure after angioplasty. The stent is placed in the dilated segment of the artery to mechanically prevent abrupt closure and restenosis. Unfortunately, even when the implantation of the stent is accompanied by aggressive and precise antiplatelet and anticoagulation therapy (typically by systemic administration), the incidence of thrombotic vessel closure or other thrombotic complication remains significant, and the prevention of restenosis is not as successful as desired. An undesirable side effect of the systemic antiplatelet and anticoagulation therapy is an increased incidence of bleeding complications, limiting its use. A suitable device would work locally to deliver a therapeutic agent that would prevent thrombus formation and inhibit smooth muscle cell proliferation without undesirable side-effects.

Stents

Recent major breakthroughs have made new materials available for percutaneous peripheral arterial and coronary artery intervention procedures. Typically, a stent is an inserted mesh of wires that stretch and mold to the arterial wall to prevent reocclusion. The arterial and coronary artery stents have made progressive structural improvements leading to the evolution of third generation stents or coated stents. Stents are described for instance in U.S. Pat. Nos. 6,235,053; 6,165,209; 6,129,725; 6,241,760; and 6,197,047.

Implantable medical devices capable of delivering medicinal agents have been described. Several patents are directed to devices utilizing biodegradable or bioresorbable polymers as drug containing and releasing coatings, including U.S. Pat. Nos. 4,916,193; 4,994,071; and 6,096,070. Other patents are directed to the formation of a drug containing hydrogel on the surface of an implantable medical device, these include U.S. Pat. Nos. 5,221,698; and 5,304,121. Still other patents describe methods for preparing coated intravascular stents. U.S. Pat. No. 5,464,650 describes coating stents via application of polymer solutions containing dispersed therapeutic material to the stent surface followed by evaporation of the solvent. U.S. Pat. No. 6,099,561 describes stents with ceramic-like coatings. U.S. Pat. No. 6,231,600 describes stents with hybrid coatings including a time released restenosis inhibiting coating and a non-thrombogenic coating to prevent clotting on the device. U.S. Pat. No. 6,214,901 describes a biocompatible polymer suitable for coating implantable medical devices and delivering therapeutics suspended therein. Additional coatings for medical devices are described for instance in U.S. Pat. Nos. 6,071,305; 6,179,817; and 6,218,016.

Several therapeutic agents have been proposed for treating or preventing restenosis. U.S. Pat. No. 6,214,868 describes preventing or treating coronary restenosis which comprises administering an effective amount of a catechin, derived from a green tea extract. US Patent No. describes inhibiting restenosis with a peptide abundant in basic amino acid residues linked via its C-terminus to a peptide of at least two consecutive hydrophobic amino acid residues. U.S. Pat. No. 6,239,118 describes inhibiting restenosis with a substituted adenine derivative such as 2-chloro-deoxyadenisine. U.S. Pat. No. 6,171,609 describes inhibiting restenosis with an inhibitor of vascular smooth muscle cell contraction. U.S. Pat. No. 6,241,718 describes inhibiting restenosis by applying cryogenic energy to a treatment site. U.S. Pat. No. 6,156,350 describes inhibiting restenosis by flushing with a solution with a pH below 4.0 such as a hydrochloric acid.

Pulmonary Hypertension

Pulmonary hypertension has been an enigma to the medical profession both diagnostically and therapeutically. Its well known "mirror image cousin," arterial hypertension is probably the most diagnosed and treated medical condition, while this poor relation remains undiagnosed, untreated and quietly deadly. Unlike arterial hypertension, pulmonary hypertension can not be readily diagnosed such as by a sphygmomanometer.

Pulmonary hypertension is defined when the pressure in the pulmonary artery exceeds 25 mm of mercury at rest or 30 mm of mercury during exercise. There are two forms of pulmonary hypertension. One is known as primary pulmonary hypertension where the cause is unknown and second form is referred to as secondary pulmonary hyertension, meaning that it is secondary to another identifiable underlying cause.

Pulmonary hypertension usually occurs in young adults, with a mean age of 45, varying from 15 to 66 years of age. Approximately 62% are female. The median survival time after diagnosis is approximately 2.5 years. Secondary pulmonary hypertension can result from a multitude of diseases including cardiac problems such as sever mitral stenosis, severe aortic stenosis, left to right shunts (VSD), congestive heart failure, diastolic dysfunction, to list a few of the cardiac causes. Other causes are obstructive sleep apnea, chronic pulmonary emboli, pulmonary parenchymal disease such as emphysema, pulmonary fibrosis or chest wall deformities. It also occurs in connective tissue disease e.g. lupus erythematosus, polymiositis, rheumatoid arthritis, scleroderma and with the CREST syndrome. Secondary pulmonary hypertension has been associated with portal hypotension, and with the use of appetite suppressants.

Elevated pulmonary artery pressure has been found to be a specifically significant prognostic factor in chronic obstructive pulmonary disease patients receiving long term oxygen therapy. In a recent study at the University Hospital in Strasbourg France, Oswald-Mammosser and co-workers found that the five year survival in patient's with severe COPD with normal resting pulmonary artery pressure was 62% and in patients with elevated pulmonary artery pressure the survival was only 36%. The means of treatment for primary or secondary pulmonary hypertension are medical or surgical. At present, most of the medical treatments are experiment and are primarily related to prostacyclin analogues given either orally, inhaled or by infusion. There have also been several studies with inhaled nitrate oxide and oral endothelin receptor antagonists. None of these produced any dramatic results. WO 01/34088 discusses the use of vasoactive intestinal peptide (VIP) for treatment of pulmonary hypertension.

Surgery for treatment of pulmonary hypertension usually consists of lung transplantation, single, bilateral or heart with bilateral lung. Most patients have a waiting period of two to three years for an appropriate donor, obviating the need for many patients who succumb to pulmonary hypertension within that time. Survival at five years post-transplantation is 37-44%. At present it does not appear to be a viable treatment. The lung volume reduction procedure remains a questionable option for COPD.

Cancer

In spite of numerous advances in medical research, cancer remains the second leading cause of death in the United States. In the industrialized nations, roughly one in five persons will die of cancer. Traditional modes of clinical care, such as surgical resection, radiotherapy and chemotherapy, have a significant failure rate, especially for solid tumors. Failure occurs either because the initial tumor is unresponsive, or because of recurrence due to regrowth at the original site and/or metastases. Even in cancers such as breast cancer where the mortality rate has decreased, successful intervention relies on early detection of the cancerous cells. The etiology, diagnosis and ablation of cancer remain a central focus for medical research and development.

Neoplasia resulting in benign tumors can usually be completely cured by removing the mass surgically. If a tumor becomes malignant, as manifested by invasion of surrounding tissue, it becomes much more difficult to eradicate. Once a malignant tumor metastasizes, it is much less likely to be eradicated.

The three major cancers, in terms of morbidity and mortality, are colon, breast and lung. New surgical procedures offer an increased survival rate for colon cancer. Improved screening methods increase the detection of breast cancer, allowing earlier, less aggressive therapy. Numerous studies have shown that early detection increases survival and treatment options. Lung cancer remains largely refractory to treatment.

Excluding basal cell carcinoma, there are over one million new cases of cancer per year in the United States alone, and cancer accounts for over one half million deaths per year in this country. In the world as a whole, the five most common cancers are those of lung, stomach, breast, colon/rectum, and uterine cervix, and the total number of new cases per year is over 6 million. Only about half the number of people who develop cancer die of it.

Vasodilators

Vasodilators cause vasodilation of or in increased rate of blood flow through the arteries. Thus, upon administration of VIP and/or NP, vasodilation or rate of blood flow would be expected to increase.

Vasoactive Intestinal Peptide

VIP is a basic, linear 28 amino acid polypeptide isolated initially form porcine duodenum (Mutt et al. (1974) Eur. J. Biochem. 42:581-589) and widely found in the central and peripheral nervous systems and digestive tract. VIP has strong vasodilating properties and hypotensive activity and systemic vasodilatory activity. Administered intravenously (IV) or directly into the heart, VIP increases heart rate and contractile force. Anderson et al. (1988) J. Cardio. Pharmacol. 12:365-371; Rigel et al. (1988) Am. J. Physiol. 255:H317-319; Karasawa et al. (1990) Eur. J. Pharmacol. 187:9-17; and Unverferth et al. (1985) J. Laboratory. Clin. Med. 106:542-550.

The amino acid structure of VIP was clarified in 1974, and since this structure is similar to both secretin and glucagons, VIP is considered to be a peptide hormone belonging to the glucagons-secretin family. Other members of this family of structurally related peptides include gastric inhibitory peptide (GIP), growth hormone releasing factor (GHRF) and adenylate cyclase-activating peptide (PACAP). Like all secretory peptides, VIP is derived by proteolytic cleavage from a larger precursor molecule. The 170 amino acid precursor preproVIP contains histidine isoleucine, another biologically active peptide. Itoh et al. (1983) Nature 304:547-549. VIP contains at least two functional regions: a region of receptor-specific binding and a region involved in biological activity. Gozes et al. (1989) Mol. Neurobiol. 3:201-236.

VIP mediates or modulates several basic cell functions. These include brain activity, endocrine functions, cardiac activity, respiration, digestion and sexual potency. The widespread physiologic distribution of VIP correlates with its involvement in a broad spectrum of biological activities. The actions of VIP are of a complex nature, encompassing receptor modulation, inducting release of neurotrophic factors, neurotransmission and neuromodulation. VIP occurs widely in the central and peripheral nervous systems and digestive tract, and may play a role in parasympathetic responses in the trachea and gastrointestinal tract.

VIP is an important modulator of cell growth, differentiation and survival during development of the sympathetic nervous system. VIP acts as a neuromodulator in several responses. Ferron et al. (1985) Proc. Natl. Acad. Sci. USA 82:8810-8812; and Kawatani et al. (1985) Science 229:879-881. In cholinergic studies VIP has a selective effect on muscarinic excitation in sympathetic ganglia with no apparent effect on nicotinic responses, indicating that VIP has intrinsic properties affecting electrical activity and also interacts with other neurotransmitter systems to modulate physiologic responses.

VIP has been found in glial cells and appears to be of physiological importance. VIP mediates communication between neurons and glia, a relationship of fundamental importance to neurodevelopment and function.

VIP immunoreactive fibers are present in and appear to be intrinsic to the canine heart. Weihe et al. (1981) Neurosci. Let. 26:283-288; and Weihe et al. (1984) Cell Tiss. Res. 236:527-540. VIP-containing neurons are present in canine hearts where VIP exerts a strong global myocardial effect similar to, but more sustained than, the adrenergic effect. The effect is qualitatively similar to other inotropic drugs that act through specific cell surface membrane receptors coupled to adenylate cyclase, for example β-adrenergic agonists such as proterenol.

VIP receptors are found in both canine and human hearts, thus canines are an appropriate model for VIP in humans. Vagal, efferent stimulation of β-blocked, atropinized dogs increased heart rate and contractile force, an effect that may be due to the release of VIP. Rigel et al. (1984) Am. J. Physiol. 246 (heart circ. physiol. 15) H168-173. VIP is released from dog atria when parasympathetic nerves are stimulated. Hill et al. (1993) J. Auton. Nerv. Sys. 43:117-122; and Hill et al. (1995).

Many different potential therapeutic uses of VIP, VIP analogues and VIP-like polypeptides have been proposed. Due to the widespread distribution and variety of activities of VIP, VIP analogues and VIP-like peptides have been proposed as treatment for various conditions including, among others, asthma and erectile dysfunction.

VIP is active when present in amounts of only picograms, and is stable in solution. This makes it particularly suited for use in a medicinal context.

VIP has inotropic and chronotropic effects due to its vasodilatory properties. VIP acts as a bronchodilator and a relaxant of pulmonary vascular smooth muscle. The inotropic state of the ventricle may be affected by the activation of several receptors, some of which are coupled to adenylate cyclase. Foremost among these is the β-adrenergic receptor, which, when activated by its corresponding neurotransmitter norepinephrine, mediates increased cardiac contractility.

Additional positive inotropic cardiac receptor pathways have been identified although physiologic roles have not yet been established. These include pathways that respond to β-adrenergic agonists including histamine, serotonin, enkephalins and VIP. Of these, VIP is a potentially important agonist because it is present in nerve fibers in the heart, is coupled to adenylate cyclase, and, when administered IV, mediates both increased contractility and coronary vasodilation. There is some evidence that VIP has two discrete binding sites specific to the central nervous system.

The time-course of chronotropic effects of VIP is dose-dependent; however the time-course for recovery from inotropic effects is not. This may be due to variation in neurotransmitter levels in extracellular spaces, occurring due to heart movement. At a constant level of sympathetic nerve stimulation, dogs whose hearts were paced at different rates showed different recovery times from the inotropic response. Thus the recovery from VIP inotropic effects is affected by heart rate, which in turn is altered by the chronotropic effects. The inotropic and chronotropic effects of VIP are therefore related but do not occur through the same mechanism. There may be different receptors for the two responses or the biochemical cascade initiated differs for the two.

Intact endothelium is necessary to achieve vascular relaxation in response to acetylcholine. The endothelial layer modulates autonomic and hormonal effects on the contractility of blood vessels. In response to vasoactive stimuli, endothelial cells release short-lived vasodilators called endothelium-derived relaxing factor (EDRF) or endothelium-derived contracting factor. Endothelial cell-dependent mechanisms are important in a variety of vascular beds, including the coronary circulation.

The natural properties of VIP have been improved. The C-terminus holds a receptor recognition site, and the N-terminus holds the activation site with minimal binding capacity. These are essential to VIP function. Peptides non-essential to function have been manipulated and altered, resulting in some cases in increased levels of activity over natural VIP. These VIP analogues and VIP-like peptides can be utilized in any situation where VIP is effective. Some VIP analogues have improved storage properties and increased duration of action, and therefore may be superior drugs. EP A 0613904; and U.S. Pat. Nos. 4,737,487; 5,428,015; and 5,521,157. VIP antagonists alter VIP function. U.S. Pat. No. 5,217,953.

VIP innervation has been demonstrated in the airways and pulmonary vessels (Dey et al. (1981) Cell Tiss. Res. 220:231-238), and the lungs are believed to be an important physiological target for VIP. The rat and guinea pig brains have VIP-specific receptor sites. Taylor et al. (1979) Proc. Natl. Acad. Sci. USA 76:660-664; Robberecht et al. (1978) Eur. J. Biochem. 90:147-154. The receptor-molecule complex has been identified in the intestine and lung. Laburthe et al. (1984) Eur. J. Biochem. 139:181-187; and Paul et al. (1985) Regul. Peptide 3:S52. Two classes of receptors with different pharmacological properties have been detected in rat lung and in human colonic adenocarcinoma cells. Atthi et al. (1988) J. Biol. Chem. 263:363-369; and El Baatari et al. (1988) J. Biol. Chem. 263:685-689.

cDNAs encoding rat and human VIP receptors have been cloned; at least one of these receptors is structurally related to the secretin receptor; at least one of these receptors is structurally related to the secretin receptor. Ishihara et al. (1992) Neuron; Sreedharan et al. (1993) Biochem. Biophys. Res. Comm. 193:546-553; and Sreedharan et al. (1995) Proc. Natl. Acad. Sci. USA 92:2939-2943. mRNA for this VIP has been found in several tissues including liver, lung, intestine and brain. mRNA for another VIP receptor has been found in stomach, testes and brain.

The VIP receptor or receptors may be coupled to adenylate cyclase, as a VIP-stimulated adenylate cyclase has been identified in various areas of the central nervous system as well as the liver and pituitary. Quick et al. (1978) Biochem. Pharmacol. 27:2209-2213; Deschodt-Lanckman et al. (1977) FEBS Lett. 83:76-80; and Rostene (1984) Progr. Neurobiol. 22:103-129. Studies of rat sensory neurons show that VIP transcription may be increased via activation of cellular transcription factors that bind to a cyclic adenosine monophosphate (cAMP) responsive element. Dobson et al. (1994) Neurosci. Lett. 167:19-23; Tsukada et al. (1987) J. Biol. Chem. 262:8743-8787; and Giladi et al. (1990) Brain Res. Mol. 7:261-267.

VIP action on cAMP may be mediated via G-proteins, signal transducers that stimulate hydrolysis of GTP to GDP, as GTP and its analogues inhibit VIP-receptor binding and potentiate cAMP synthesis in response to VIP. Paul (1989) Biochem. Pharmacol. 38:699-702. If the VIP-receptor is coupled to G-proteins, this could explain the array of VIP effects found, as G-proteins are widespread and involved in several signal transduction pathways. VIP induces its own mRNA in PC12 cells, probably as a result of its activation of adenylate cyclase. Tsukada et al. (1995) Mol. Cell. Endocrinol. 107:231-239. Regulation of VIP expression occurs also at a translational or post-translational level. Agoston et al. (1992). VIP may act as an autocrine regulator of its own synthesis.

VIP treatment produces a loss of responsiveness to subsequent rechallenges; a short-term exposure to VIP results in internalization of the receptor-peptide complex, a feature that may be tissue-specific. Rosselin et al. (1988) Ann. NY Acad. Sci. 527:220-237; Boissard et al. (1986) Cancer Res. 46:4406-4413; and Anteunis et al. (1989) Am. J. Physiol. 256:G689-697. After internalization, VIP is degraded in lysosymes and may serve as an intracellular effector, while the receptors are recycled to the cell surface.

VIP binding sites and VIP-stimulated adenylate cyclase can be reduced by preincubation with different agents, although the different agents appear to function by different mechanisms. Turner et al. (1988) J. Pharmacol. Exp. Ther. 247:417-423. The VIP receptor appears to be translocated to a light vesicle fraction after such exposure. In some cell lines, the half-life of the receptor was around 2 days, and N-glycosylation was necessary for translocation. An internalized VIP receptor is dissociated from adenylate cyclase activity, although the internalization process is not completely independent of cAMP accumulation. Hejblum et al. (1988) Cancer Res. 48:6201-6210. VIP signal transduction thus relies on multiple pathways other than elevation of cAMP.

Neuropeptide

Neuropeptide Y (NPY) is a 36-amino acid peptide neurotransmitter that is located throughout the central and peripheral nervous systems. Tatemoto (1982) Proc. Natl. Acad. Sci. USA 79:5485; and Hazlewood (1993) Proc. Soc. Exp. Biol. Med. 202:44. It affects a broad range of phenomena, including blood pressure regulation, memory, anxiolysis/sedation, food and water appetite, vascular and other smooth muscle activity, intestinal electrolyte secretion, and urinary sodium excretion. Colmers and Wahlestedt, The Biology of Neuropeptide Y and Related Peptides (Humana Press, Totowa, N.J. 1993).

Peptide YY (PYY) is also a 36 amino acid peptide and has significant sequence homology (70%) to NPY. Tatemoto et al. (1982) Nature 296:659. Its anatomical distribution is similar to that of NPY, although it is located mainly in the endocrine cells of the lower gastrointestinal tract. Bottcher et al. (1984) Regul. Pept. 8:261 (1984). Like NPY, PYY stimulates feeding in rats. Morley et al. (1985) Brain Res. 341:200. Along with the pancreatic polypeptide (PP), NPY and PYY have a common tertiary structure, characterized by the so-called PP-fold. Glover (1985) Eur. J. Biochem. 142:379. Both NPY and PYY show about a 50% sequence homology with PP.

Because of their structural similarities, NPY and PYY have a number of common receptors. At least four receptor subtypes, Y1, Y2, Y3, and Y4/PP, have been identified. The affinity for NPY, PYY, and various fragments thereof varies among the subtypes. WO 95/17906. As used herein, NP encompasses all forms of neuropeptides with stenosis-inhibiting activity.

OBJECTS AND SUMMARY OF THE INVENTION

The present invention encompasses a device containing a delivery system for implantation in a biological lumen and a therapeutically effective amount a pharmaceutical agent. The device is particularly useful for delivery of a pharmaceutical agent locally for instance of vasoactive intestinal peptide effective to treat stenosis in the blood vessel or proximal to a solid tumor to deliver chemotherapy directly to the vasculature of the tumor. The lumen can be any suitable physiologic lumen including, without limitation, an artery, a blood vessel, bone marrow, the pancreatic duct, the ureter, a urethra, the bile duct and the spinal column. The delivery system can be any known in the art including, but not limited to, a stent. The device need only be the general shape of a stent however in that it has a lumen and can be placed in a biologic lumen. The device need not provide the rigidity of a stent as it is not necessarily provided to maintain the lumen size of an angioplasty stent.

The device can be, and preferably, is biodegradable or bioresorbable. In the case of such stents, replacement as needed is provided. For instance, in the case of prevention of restenosis, a single stent with a drug delivery life of 3-6 months should be sufficient to treat restenosis. A stent or similar device that is resorbed or degraded within this time would be sufficient. In treating pulmonary hypertension, however, replacement stents would ensure continuous treatment of the disease. A device that could be resorbed or degraded and replaced every few months would greatly improve the treatment profile of these patient. Methods of placing stents are well known in the art and the preferred locations of placement are likewise known in the art.

In some circumstances, a biodegradable or bioresorbable catheter or stent provides the properties necessary for drug delivery according to the invention. If the stent is permanent, the pharmaceutical agent can be coated onto or impregnated into the stent. Numerous stents are known in the art, including, but not limited to, those discussed in the Background of the Invention. Additional suitable stents are mentioned for instance in U.S. Pat. Nos. 6,387,124; 6,387,035; 6,383,215; 6,378,382; 6,372,723; 6,368,356; 6,358,989; 6,355,640; 6,352,682; 6,350,764; 6,344,486; 6,399,072; 6,338,739; 6,338,709; 6,306,074; 6,290,949; 6,287,332; 6,273,913; 6,273,908; 6,261,630; 6,261,320; 6,258,121; 6,254,628; 6,251,920; 6,248,129; 6,235,778; 6,176,871; 6,176,871; 5,593,974; and U.S. Patent Application Ser. Nos. 2002/0065552; 2002/0061326; 2002/0055710; 2002/0055666; 2002/0052572; 2002/0049162; 2002/0042645; 2002/0032414; 2002/0029052; 2002/0002353; 2001/0034352; and 2001/0009911.

In one embodiment, the device provided herein provides a drug eluting stent that inhibits intimal cell proliferation, reverses endothelial dysfunction, enhances the microcirculation and prevents or inhibits negative remodeling. The device is suitable for use in treatment of decreased blood flow through a blood vessel such as is found in pulmonary hypertension, restenosis and diabetes. Thus, the device is suitable for use in treating each of these indications.

It has been demonstrated in multiple clinical studies that angioplasty is more effective than thrombolytic therapy in reestablishing flow in acute/subacute myocardial infarction. The device is suitable for use in treating pulmonary hypertension, acute/subacute infarction, or severe stenosis causing ischemia, the so-called rescue angioplasty. The stent is suitable for use in treating any patient in danger of suffering stenosis of a blood vessel or pulmonary hypertension.

Where used for treating restenosis, the device has many advantages over ordinary stents in ameliorating stenosis. Restenosis is induced by initial platelet adhesion and thrombus formation followed by immunocyte adhesions on the stent surface and injured vessel wall. The thrombus then releases factors that activate proliferation of smooth muscle cells. The pharmaceutical agents employed with the device of the present invention elevate platelet cAMP levels and inhibit the platelet activation induced by platelet activating factor. By administering the pharmaceutical agent directly to the site of stenosis, the device decreases side effects and allows for use of much lower drug concentrations than would be used in systemic administration. Due to the nature of vasodilators such as VIP and NP, systemic administration would be contraindicated in treating or preventing stenosis.

In another embodiment, the device is suitable for use in delivering a chemotherapeutic agent to a tumor. The device can be implanted in an artery that feeds the vasculature of the tumor. Thus, the device is implanted proximal to a tumor. This decreases systemic levels of chemotherapeutic agents and increases the concentration of agent delivered directly to the tumor. Any suitable tumor can be treated including, but not limited to, astrocytoma, oligodendroglioma, ependymoma, medulloblastoma, primitive neural ectodermal tumor (PNET), pancreatic ductal adenocarcinoma, small and large cell lung adenocarcinomas, squamous cell carcinoma, bronchoalveolarcarcinoma, epithelial adenocarcinoma, and liver metastases thereof, hepatoma, cholangiocarcinoma, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, soft tissue sarcomas and leiomyosarcomas.

The device is also useful for treating pancreatic disorders and can be placed in the pancreatic duct. In this instance, a biodegradable or bioresorbable device is preferred. The device is also suitable for use when placed in other lumens including, but not limited to, ureter, urethra, bile duct and spinal column for deliver of pharmaceutical agents to these sites.

The dose of the pharmaceutical agent required to be administered to achieve the desired effect of improvement in the patient's condition will vary depending on several factors, including the severity of symptoms, size and health of the patient and elapsed time since onset of infarction, ischemia or angioplasty. The preferred amount to be administered depends on the pharmaceutical agent, patient and the circumstances.

The appropriate dosage range is that which is large enough to produce amelioration but not so large as to induce unwanted side effects. The required dosage can be determined by one of skill in the art. Preferably, when the pharmaceutical agent is VIP, it is present in the range of from about 0.001 µg to 500 µg. More preferably, the VIP is present in an amount of from about 1 µg to 250 µg. Preferably, when the pharmaceutical agent is NP, it is present in the range of from about 0.001 µg to 500 µg. More preferably, the NP is present in an amount of from about 1 µg to 250 µg. If VIP and NP are used in combination, the concentrations of one or both are adjusted accordingly. Any concentration of the named pharmaceutical agents effective to ameliorate (prevent, inhibit or treat) restenosis is encompassed by the invention.

As used herein, "VIP" and "NP" refer to the native molecules and derivatives thereof. VIP and NP encompass any natural or synthetic peptide that is substantially similar to the native peptide and retains native activity even though the peptide may have been manipulated, genetically or otherwise, to alter or enhance that activity. "Substantially similar" means a peptide in which amino acid residues non-essential to the stenosis-inhibition activity of the peptide have been altered in an attempt to alter or enhance that activity, but the peptide still retains a high level of amino acid residue sequence similarity to the native peptide. VIP is advantageous because it is a vasodilator; a vasorelaxant (it decreases systemic vascular resistance (SVR)); an anti-inflammatory, it inhibits mitogen induced T lymphocyte proliferation; inhibits cytokine release; decreases Interleukin-2 production; inhibits vascular smooth muscle cell growth; and enhances endothelial constitutive nitric oxide synthetase (ecNOS) an enzyme for generating nitric oxide (NO) in endothelial cells. NP is advantageous because it is a potent vasodilator (200 times more than prostacyclin); a vasorelaxant; an anti-inflammatory, and inhibits mitogen induced The lymphocyte proliferation; inhibits cytokine release; decreases Interleukin-2 production; enhances ecNOS; inhibits platelet aggregation increasing cAMP in platelets and therefore lessens platelet aggregation. It also lessens platelet aggregation by inhibiting phospholipase A2 activity.

Suitable chemotherapeutic agents include, without limitation, vinca alkaloids such as the vinblastine, vincristine and vindesine sulfates, adriamycin, bleomycin sulfate, carboplatin, cisplatin, cyclophosphamide, cytarabine, dacarbazine, dactinomycin, duanorubicin hydrochloride, doxorubicin hydrochloride, etoposide, fluorouracil, lomustine, mechlorethamine hydrochloride, melphalan, mercaptopurine, methotrexate, mitomycin, mitotane, pentostatin, pipobroman, procarbaze hydrochloride, streptozotocin, taxel paclitaxel (TAXOL®), thioguanine, uracil mustard and anti-cancer antibodies.

"Amelioration" means any improvement in the condition of the patient that has occurred as a result of administration of treatment with the claimed invention. This includes any increase in survival time over what would have previously been expected. In a patient responding particularly well there should be some restoration of effective cardiac function. It does not mean a complete cure or prevention of all restenosis although this is what is aimed for.

A "patient" is a vertebrate, preferably mammal, more preferably human. Mammals including, but not limited to, humans, farm animals, sport animals and pets. Preferably, the patient is human. Suitable patients for treatment with this invention are those suffering from arterial stenosis arising by any means.

The pharmaceutical agents can be delivered by the delivery system by any method known in the art. For instance, the agent can be coated or adsorbed on the delivery system. Any biocompatible coating known in the art, including, but not limited to, those discussed in the Background of the Invention, can be used provided it releases the pharmaceutical agent in a therapeutically effective manner. The biocompatible coatings are typically polymers with their tertiary structure acting as a depot for a drug to be held and released by the characteristics of the coating or elution of the drug from a coating. Suitable coatings also include saccharides and polysaccharides. Numerous coatings and solid dose delivery compositions are provided by Roser et al. WO 96/03978. Preferably, the device is biodegradable or bioresorbable and allows for near zero order release rate of the agent.

Suitable materials for use in making or coating the device include, without limitation, reducing, non-reducing and hydrophobically derivatized carbohydrates. Reducing carbohydrates include, without limitation glucose, maltose, lactose, fructose, galactose, mannose, maltulose, iso-maltulose and lactulose. Non-reducing carbohydrates include, without limitation, trehalose, raffinose, stachyose, sucrose and dextran. Other useful carbohydrates include non-reducing glycosides of polyhydroxy compounds selected from sugar alcohols and other straight chain polyalcohols. The sugar alcohol glycosides are preferably monoglycosides, in particular the compounds obtained by reduction of disaccharides such as lactose, maltose, lactulose and maltulose. Hydrophobically derivatized carbohydrates refer to a wide variety of carbohydrates where at least one hydroxyl group is substituted with a hydrophobic moiety including, but not limited to, esters and ethers. Numerous examples of suitable carbohydrates and their syntheses are described in Developments in Food Carbohydrate—2 ed. C. K. Lee, Applied Science Publishers, London (1980). Other syntheses are described for instance, in Akoh et al. (1987) J. Food. Sci. 52:1570; Khan et al. (1993) Tetra. Letts 34:7767 Khan (1984) Pure & Appl. Chem. 56:833-844; and Khan et al. (1990) Carb. Res. 198:275-283. Such carbohydrates include, without limitation, sorbitol hexaacetate, α-glucose pentaacetate, β-glucose pentaacetate, 1-0-Octyl-β-D-glucose tetraacetate, trehalose octaacetate, and di-0-methyl-hexa-0-acetyl sucrose.

Whichever method is used coating or impregnation of pharmaceutical agent, it should allow slow release of a therapeutically effective amount of the pharmaceutical agent for a therapeutically effective length of time. For instance, slow release by diffusion into the lumen of a local artery or duct is effective. Of course, drug dissolution into the wall of the lumen will occur and account for some of the therapeutic affect. The pharmaceutical agents can also be bonded onto the surface of the delivery system and released by chemical interaction with the blood and its components or other physiologic fluids.

The pharmaceutical agent can be formulated with other physiologically acceptable components. Such formulations can contain appropriate non-toxic and non-interfering components. Such components including, but not limited to, liquid excipients, medicinal agents, pharmaceutical agents, carriers and substances such as wetting or emulsifying agents and pH buffering agents. Liquid excipients including, but not limited to, water, saline glycerol or ethanol.

All references cited herein, both supra and infra, are hereby incorporated herein by reference. Although the foregoing invention has been described in some detail by way of illustration and example for the purposes of clarity and understanding, it will be apparent to those skilled in the art that certain changes and modifications can be practiced. Therefore, the description and examples should not be construed as limiting the scope of the invention, which is delineated by the appended claims.

The invention claimed is:

1. A device comprising a drug delivery system for implantation in a lumen of a physiologic conduit, an amount of vasoactive intestinal peptide effective to cause vasodilation, and an amount of a chemotherapeutic agent effective to treat a condition responsive to the chemotherapeutic agent proximal to the physiologic conduit and/or distal to the physiologic conduit.

2. The device according to claim 1, wherein the delivery system is a stent or catheter.

3. The device according to claim 1, wherein the physiologic conduit is selected from the group consisting of artery, bone marrow, pancreatic duct, ureter, urethra, bile duct and spinal column.

4. The device according to claim 3, wherein the physiologic conduit is a pulmonary, cranial, femoral, or coronary artery.

5. The device according to claim 1, wherein the vasoactive intestinal peptide is present in an amount effective to increase blood flow proximal to and distal to the site of implantation.

6. The device according to claim 1, wherein the vasoactive intestinal peptide is present in an amount of from about 1 μg to 500 μg.

7. The device according to claim 1, wherein the chemotherapeutic agent is selected from the group consisting of vinca alkaloids, vinblastine, vincristine, vindesine sulfates, adriamycin, bleomycin sulfate, carboplatin, cisplatin, cyclophosphamide, cytarabine, decarbazine, dactinomycin, duanorubicin hydrochloride, doxorubicin hydrochloride, etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, paclitaxel, thioguanine, uracil mustard and anti-cancer antibodies.

8. The device according to claim 7, wherein the device is implanted proximal to a tumor.

9. The device according to claim 8, wherein the tumor is selected from the group consisting of astrocytoma, oligodendroglioma, ependymoma, medulloblastoma, primitive neural ectodermal tumor (PNET), pancreatic ductal adenocarcinoma, small and large cell lung adenocarcinomas, squamous cell carcinoma, bronchoalvcolarcarcinoma, epithelial adenocarcinoma, and liver metastases thereof, hepatoma, cholangiocarcinoma, breast tumors, ductal and lobular adenocarcinoma, squamous and adenocarcinomas of the uterine cervix, uterine and ovarian epithelial carcinomas, prostatic adenocarcinomas, transitional squamous cell carcinoma of the bladder, soft tissue sarcomas and leiomyosarcomas.

10. The device according to claim 1, wherein the chemotherapeutic agent is coated on the delivery system.

11. The device according to claim 1, wherein the chemotherapeutic agent is impregnated into the delivery system.

12. The device according to claim 1, wherein the device is biodegradable or bioresorbable.

* * * * *